(12) United States Patent
Yamazaki et al.

(10) Patent No.: US 8,496,877 B2
(45) Date of Patent: Jul. 30, 2013

(54) AUTOMATIC ANALYZER

(75) Inventors: Isao Yamazaki, Ryugasaki (JP); Ryuji Tao, Hitachinaka (JP); Katsuaki Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/529,395

(22) Filed: Jun. 21, 2012

(65) Prior Publication Data
US 2012/0258012 A1      Oct. 11, 2012

Related U.S. Application Data

(63) Continuation of application No. 10/614,105, filed on Jul. 8, 2003, now abandoned.

(30) Foreign Application Priority Data

Jul. 10, 2002   (JP) ................. 2002-200724

(51) Int. Cl.
| | | |
|---|---|---|
| *G01N 21/00* | (2006.01) | |
| *G01N 30/04* | (2006.01) | |
| *G01N 35/00* | (2006.01) | |
| *G01N 35/08* | (2006.01) | |

(52) U.S. Cl.
USPC ............... 422/67; 422/62; 422/63; 422/64; 422/65; 422/66; 436/43; 436/47; 436/50; 436/51; 436/54; 436/55

(58) Field of Classification Search
None
See application file for complete search history.

(56) References Cited

U.S. PATENT DOCUMENTS

| | | |
|---|---|---|
| 4,234,538 A | 11/1980 | Ginsberg et al. |
| 4,276,051 A | 6/1981 | Ginsberg et al. |
| 4,808,380 A | 2/1989 | Minekane |
| 5,051,238 A | 9/1991 | Umetsu et al. |
| 5,445,037 A | 8/1995 | Itoh |
| 6,019,945 A | 2/2000 | Ohishi et al. |

FOREIGN PATENT DOCUMENTS

| | | |
|---|---|---|
| EP | 0 898 171 | 2/1999 |
| JP | 04-106472 | 4/1992 |
| JP | 5-10957 | 1/1993 |
| JP | 07-198725 | 8/1995 |
| JP | 8-5639 | 1/1996 |
| WO | 93/20440 | 10/1993 |

*Primary Examiner* — Neil N Turk
(74) *Attorney, Agent, or Firm* — Mattingly & Malur, PC (57) ABSTRACT

An automatic analyzer according to the present invention is compact, mounting great number of reagents, having high processing ability. Reagent disks are arranged at inside and outside of a reaction disk. A reagent probe can inject a reagent into the position which is common position of both reagent disks. One of plural reagent probes approaches to one of reagent disks at one cycle. Plural reagent probes alternatively approach to the reagent disk. Therefore, the first reagents and the second reagents can be placed on both reagent disks. The mounting number of reagents can be increased without enlarging an analyzer. The cycle time can be shortened to make an automatic analyzer to have high processing ability.

3 Claims, 5 Drawing Sheets

AUTOMATIC ANALYZER

CROSS-REFERENCE

This application is a continuation application of U.S. Ser. No. 10/614,105, filed Jul. 8, 2003, the entire contents of which are hereby incorporated by reference. This application claims priority to JP 2002-200724, filed Jul. 10, 2002.

BACKGROUND OF THE INVENTION

1. Field of the Invention

This invention relates to an automatic analyzer for automatically analyzing components in blood or the like, and especially to an automatic analyzer permitting a greater number of reagents thereon and having a high analytical capacity per unit time.

2. Description of the Related Art

Automatic analyzers, which automatically analyze biological samples such as blood and output results, have become indispensable for large hospitals, which receive a great number of patients, and clinical laboratories, which conduct tests by undertaking them from medium and small hospitals and doctors' offices, to perform analyses efficiently.

Desired as such automatic analyzers are those having a compact structure, permitting a variety of analyses, and having a high processing speed, and a variety of automatic analyzers have been proposed. For example, JP-A-5-10957 discloses an automatic analyzer provided with two reagent disks, which allow to mount reagents in concentric circles, and reagent probes independently movable corresponding to respective concentric trains of individual reagent containers. Namely, the reagent disks are arranged in concentric circles to increase a number of reagents to be mounted on the reagent disk. The reagent dispensing probes can move independently with each other corresponding to the respective trains of the reagent to avoid a reduction in processing speed.

SUMMARY OF THE INVENTION

According to the technology disclosed in JP-A-5-10957, however, the plural reagent probes accessing to the train of reagent containers on one reagent disk are operable about the same axis of rotation.

In this case, reagents from reagent containers on the same reagent disk can be dispensed only into reaction cells placed at the same dispensing position on the reaction disk. On the other hand, reagents from reagent containers on one reagent disk can be dispensed one position on the reaction disk, and reagents from reagent cells on the other reagent disk can be dispensed the other position different from one position on the reaction disk.

Namely, in the automatic analyzer disclosed in JP-A-5-10957, the reagent probe can suck reagents only in combinations specified by the arrangement of the reagent containers, so that analysis with a random combination of reagents cannot be performed with high handling capacity.

An object of the present invention is, therefore, to provide an automatic analyzer, which permits arrangement of reagents with a high degree of freedom on reagent disks, allows to mount a great number of reagents, and has a high analytical capacity per unit time.

The object of the present invention can be achieved by the following automatic analyzer:

An automatic analyzer having a reagent disk for arranging on a circumference thereof plural reagent containers, a reaction disk for arranging on a circumference thereof plural reaction cells, and a section for reacting the reagent in the reagent and sample in the reaction cell and for analyzing the reaction. The automatic analyzer includes plural reagent disks and a reagent dispensing probe for sucking the reagent from the reagent container and injecting the same into the reaction cell. The reagent dispensing probe sucks reagents from each of reagent containers on plural reagent disks, injecting the reagent into a reaction cell on same dispensing position on the reaction disk. This automatic analyzer can be rephrased as described below.

An automatic analyzer having a reagent disk for arranging on a circumference thereof plural reagent containers, a reaction disk for arranging on a circumference thereof plural reaction cells, and a section for reacting the reagent in the reagent and sample in the reaction cell and for analyzing the reaction. The automatic analyzer includes plural reagent disks and a reagent dispensing probe capable of dispensing a reagent to a reaction cell on the same position on the reaction disk with no movement of the reaction disk from various position of the reagent containers arranged on circumferences of the reagent disks. The expression "a reagent dispensing probe capable of dispensing . . . containers arranged on circumferences of the reagent disks" is a rephrase of the possibility that reagents can be dispensed to the same dispensing position on the reaction disk, and does not mean that the reaction is fixed to prevent its movement. The expressions "reagent disks" and "reaction disk" do not absolutely require that they are disk-shaped, so that the expression "on a circumference of a disk" is used. In the case of a disk-shaped disk, this expression may therefore be rephrased as "on a circular circumference". Further, the reagent containers may be arranged on the circular circumference of a circular disk and rotating the disk. Further, the reagent containers may be arranged on a closed-loop belt conveyor, being moved by driving the belt conveyor. In the latter instance, the movement track of the reagent containers is not required to be circular, thereby allowing to set a movement track of a desired shape.

Further, an automatic analyzer can include a plurality of independently-operable reagent dispensing each of which corresponds to each of reagent containers. The reagent dispensing probes can dispense a reagent to a reaction cell on the same position on the reaction disk with no movement of the reaction disk from various position of the reagent containers arranged on circumferences of the reagent disks. The expression "a reagent to a reaction cell . . . containers arranged on circumferences of the reagent disks" is synonymous with the existence of plural reagent dispensing positions. In other words, this expression means that the automatic analyzer includes provided with reagent dispensing probes arranged corresponding to plural reagent dispensing positions, respectively.

The reagent dispensing probes includes a moving mechanism capable of reciprocating the reagent dispensing probe along a rail extending over the plural reagent disks. The rail may be linear or curved in configuration insofar as it permits sucking of a reagent from one of the reagent containers on the plural reagent disks. Further, no limitation is imposed on the moving mechanism for each reagent dispensing probe insofar as it can move the reagent dispensing probe along the rail. For example, it is possible to adopt such a construction that the reagent dispensing probe is equipped with a motor and is arranged pendant from the rail disposed above the reagent disks such that the reagent dispensing probe is movable along the rail, or such a construction that the reagent dispensing probe is equipped with a motor and runs on the rail disposed below the reagent disks.

Further, plural reagent dispensing probes may be arranged such that they can reciprocate along a rail and further, a plurality of such rails may be arranged. The number of reagent dispensing probes arranged on one rail may desirably be the same as the number of reagent disks, because an excessively large number of reagent dispensing probes leads to mutual interference in operation between the reagent dispensing probes. An analysis can be performed faster with the number of rails. Nonetheless, it is desired to choose an adequate number of rails depending upon the kinds and numbers of reagents to be mounted, the analytical capacity, etc., because an excessively large number of rails develops a problem such that the reagent disks would be required to stop longer upon dispensing reagents.

At least one of the plural reagent disks may preferably be arranged inside the reaction disk with their central axes extending along the same line. To construct an automatic analyzer compact, its space efficiency has to be increased. The space efficiency can be improved, for example, by constructing a reaction disk in the form of a ring and arranging a disk-shaped reagent disk inside the ring. Needless to say, plural reagent disks can be arranged concentrically. Arrangement of a reaction disk and a reagent disk with their central axes extending along the same line permits a simpler mechanical structure, although they can of course be arranged with their central axes being shifted from each other as needed.

At least one of the reagent dispensing probes may be provided with a moving mechanism capable of moving the at least one reagent dispensing probe in a direction substantially vertical to the rail. This construction requires a more complex mechanism for the reagent dispensing probe, but the positional range of accessible reagent containers becomes wider, leading to an improvement in the freedom of analysis. Whether or not this mechanism is arranged should be chosen depending on its need. The reagent containers may each be constructed such that it can store in a single package both of a first reagent and a second reagent to be used for the same analysis item and can be replaced package by package.

DETAILED DESCRIPTION OF EMBODIMENTS OF THE INVENTION

Figure 1:
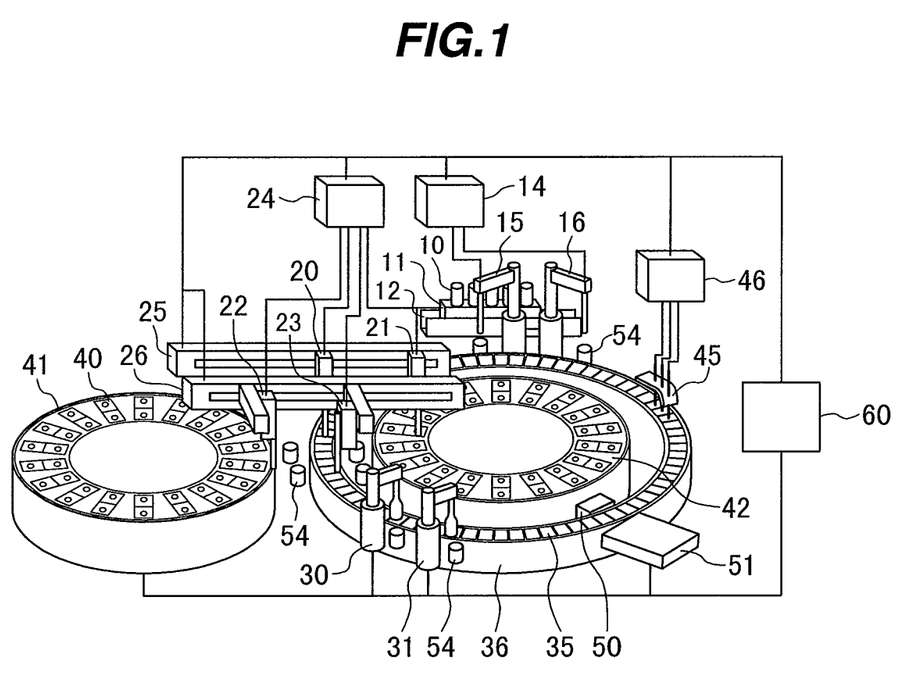
FIG. 1 is a perspective view of an automatic analyzer according to a first embodiment of the present invention.

With reference to the accompanying drawings, the embodiments of the present invention will be described hereinafter. FIG. 1 is a perspective view of the first embodiment of the present invention, FIG. 2 being a top view of the first embodiment. Fifty-four reaction cells 35 are arranged along a circular circumference of a reaction disk 36 disposed on a housing 62. A reagent disk 42 is arranged inside the reaction disk 36, a reagent disk 41 is arranged outside the reaction disk 36. The reagent disks 41,42 can each mount a plurality of reagent containers 40 along a circular circumference. Two reagents are received in one reagent container 40. In the neighborhood of the reaction disk 36, a transport mechanism 12 is arranged to move a rack 11 with sample containers 10 mounted thereon. Rails 25,26 are arranged over the reagent disks 41,42. Reagent dispensing probes 20,21 are arranged on the rail 25 moving in parallel and vertical directions relative to the rail 25. Reagent dispensing probes 22,23 are arranged on the rail 26 moving in three axis directions of the rail 26. The reagent dispensing probes 20,21,22,23 are connected to a reagent pump 24 respectively. Sampling probes 15,16 are arranged between the reaction cells 35 and the transport mechanism 12 being rotatable and movable up and down. The sampling probes 15,16 are each connected to a sampling pump 14. Around the reaction disk 36, mixing units 30,31, a light source 50, a detection unit 51 and a washing unit 45 are arranged. The washing unit 45 is connected to a washing pump 46. A washing port 54 is arranged within an operational range of the sampling probes 15,16, reagent dispensing probes 20,21,22,23 and mixing units 30,31. The sampling pump 14, reagent pump 24, washing pump 46, detection unit 51, reaction cells 35, reagent disk 41, reagent dispensing probes 20,21,22,23 and sampling probes 15,16 are each connected to a controller 60.

Figure 3:
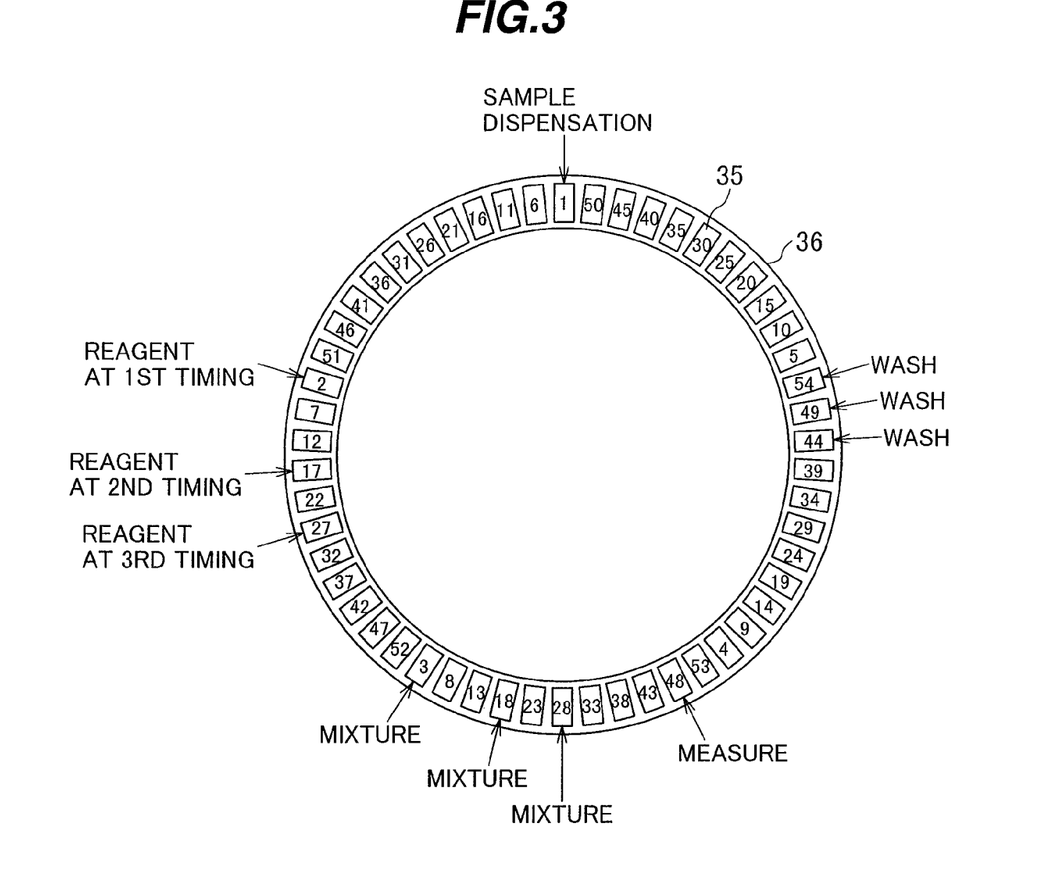
FIG. 3 is a fragmentary schematic illustration of the automatic analyzer of the first embodiment.

As illustrated in FIG. 3, a sample dispensing position, a first-timing reagent dispensing position, a second-timing reagent dispensing position, a third-timing reagent dispensing position, a mixing position, a measuring position and a washing position are set on the reaction disk 36. Using a predetermined cycle time as a unit, the reaction disk rotates counterclockwise over 11 pitches and stops. For example, a reaction cell which is located at Position 1 in a certain cycle advances to Position 2 in the following cycle.

With the automatic analyzer, an analysis is performed in the following procedure.

Figure 2:
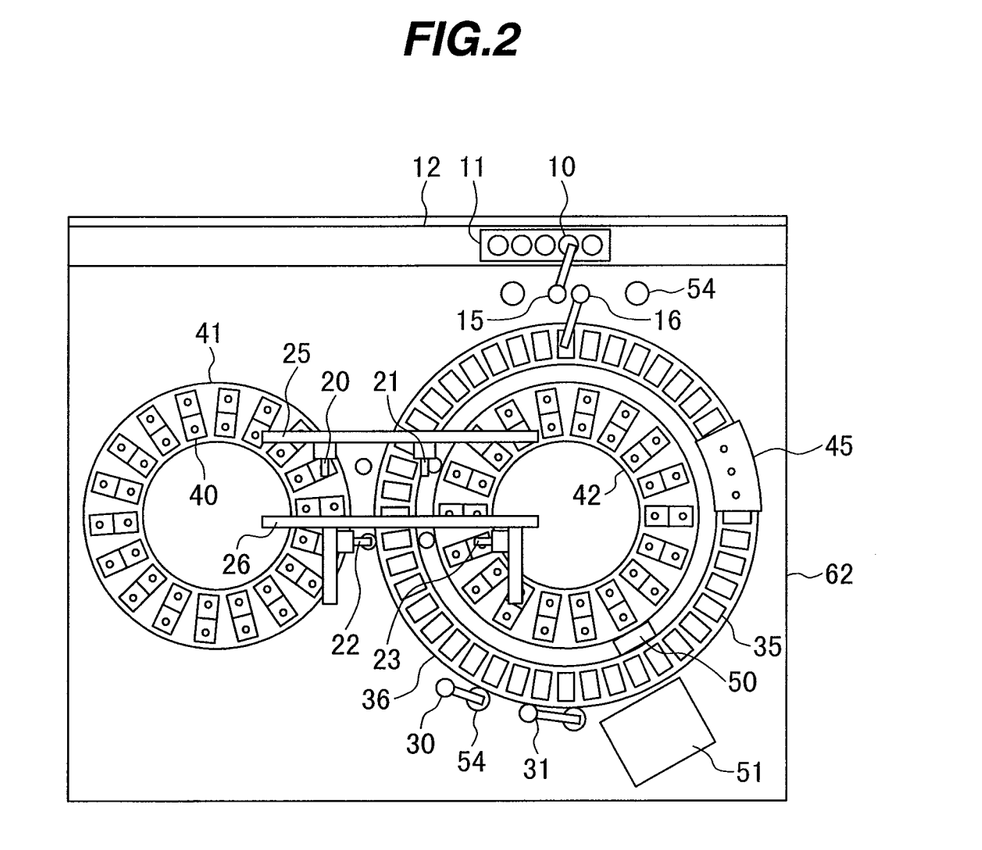
FIG. 2 is a top plan view of the automatic analyzer of the first embodiment.

Samples to be tested, such as blood samples, are received in the sample containers 10, the sample container being mounted on the rack 11, the rack 11 being conveyed by the transport mechanism 12. The sampling probe 15 firstly sucks the sample in an amount required for a first test from the sample container 10 located at a specific position. In a first cycle, a predetermined amount of the sample is injected from the sampling probe 15 into the reaction cell 35 located on the reaction disk 1 at Position 1. In the meantime, the reagent dispensing probe 20 sucks a first reagent, which corresponds to the first test in a predetermined amount, from a reagent containers 40 on the reagent disk 41.

In a second cycle, the reaction cell advances to Position 2 on the reaction disk. At this position, the reagent dispensing probe 20 injects the predetermined amount of the first reagent into the reaction cell. In the meantime, the sampling probe 15 is washed.

In a third cycle, the reaction cell advances to Position 3 on the reaction disk, and at this position, the reagent and the sample are mixed with each other by the mixing unit 30. In the meantime, the reagent dispensing probe 20 is washed.

In a fourth cycle, the reaction cell, in the course of its advance to Position 4 on the reaction disk, passes between the light source 50 and the detection unit 51 to perform an optical measurement. During the rotation of the reaction disk, the mixing unit 30 is washed in the washing port 54.

In 9th, 14th, 19th, 24th, 29th, 34th and 39th cycles, optical measurements are also performed likewise.

When the first test is designed to dispense the second reagent at a second timing, the reagent dispensing probe 22, in a 16th cycle, sucks the second reagent from the reagent container 40 on the reagent disk 41, and in a 17th cycle, the probe 22 injects the second reagent into the reaction cell located at Position 17 on the reaction disk. In an 18th cycle, the mixing unit 31 mixes the liquid in the reaction cell located at Position 18 on the reaction disk. In the meantime, the reagent dispensing probe 22 is washed.

When the first test is designed to dispense the second reagent at a third timing, the reagent dispensing probe 22, in a 26th cycle, sucks the second reagent from the reagent container 40 on the reagent disk 41, and in a 27th cycle, the probe 22 injects the second reagent into the reaction cell located at Position 27 on the reaction disk. In a 28th cycle, the mixing unit 31 the liquid in the reaction cell located at Position 28 on the reaction disk. In the meantime, the reagent dispensing probe 22 is washed.

After repeating an optical measurement subsequent to the dispensing and mixing of the second reagent, the washing unit 45, at Position 44 or 49 on the reaction disk, sucks the liquid from the reaction cell and injects a washing solution into the reaction cell in a 44th cycle and a 49th cycle, respectively. Further, in a 54th cycle, the washing solution is completely sucked.

The results of the plural optical measurements performed by the detection unit 51 are fed to the controller 60, and the controller 60 calculates the concentration of the measurement items of the first test.

In the second test, the sampling probe 16, firstly in a 1st cycle, sucks the sample in an amount required for the second test from the sample container 10 located at the specific position. In a 2nd cycle, a predetermined amount of the sample is injected from the sampling probe 16 into the reaction cell 35 located at Position 1 on the reaction disk. In the meantime, the reagent dispensing probe 21 sucks a first reagent, which corresponds to the second test, in a predetermined amount from the corresponding one of the reagent containers 40 on the reagent disk 42.

In a 3rd cycle, the reaction cell advances to Position 2 on the reaction disk. At this position, the reagent dispensing probe 21 inject the predetermined amount of the first reagent into the reaction cell. In the meantime, the sampling probe 16 is washed.

In a 4th cycle, the reaction cell advances to Position 3 on the reaction disk, and at this position, the reagent and the sample are mixed with each other by the mixing unit 30. In the meantime, the reagent dispensing probe 21 is washed.

In a 5th cycle, the reaction cell, in the course of its advance to Position 4 on the reaction disk, passes between the light source 50 and the detection unit 51 to perform an optical measurement. During the rotation of the reaction disk, the mixing unit 30 is washed in the washing port 54.

In 10th, 15th, 20th, 25th, 30th, 35th and 40th cycles, optical measurements are also performed likewise.

When the second test is designed to dispense the second reagent at the second timing, the reagent dispensing probe 23, in a 17th cycle, sucks the second reagent from the reagent container 40 on the reagent disk 42, and in an 18th cycle, the probe 23 injects the second reagent into the reaction cell located at Position 18 on the reaction disk. In a 19th cycle, the mixing unit 31 mixes the liquid in the reaction cell located at Position 18 on the reaction disk. In the meantime, the reagent dispensing probe 23 is washed.

When the second test is designed to dispense the second reagent at the third timing, the reagent dispensing probe 23, in a 27th cycle, sucks the second reagent from the corresponding reagent container 40 on the reagent disk 42, and in a 28th cycle, the probe 23 injects the second reagent into the reaction cell located at Position 27 on the reaction disk. In a 29th cycle, the mixing unit 31 mixes the liquid in the reaction cell located at Position 28 on the reaction disk. In the meantime, the reagent dispensing probe 23 is washed.

After repeating the optical measurement subsequent to the dispensing and mixing of the second reagent, the washing unit 45, at Position 44 or 49 on the reaction disk, sucks the liquid from the reaction cell and injects a washing solution into the reaction cell in a 45th cycle and a 50th cycle, respectively. Further, in a 55th cycle, the washing solution is completely sucked.

The results of the plural optical measurements performed by the detection unit 51 are fed to the controller 60, and concentrations of measurement items in the second test are calculated.

In a third test, the same steps as in the first test are repeated with a delay of 2 cycles. In the fourth test, the same steps as in the second test are repeated with a delay of 2 cycles. Similar steps are then repeated successively, and in plural tests, concentrations of measurement items in samples are analyzed.

In this embodiment, the reagent dispensing probe 20 approaches or accesses to the reagent disk 41 in an odd-numbered cycle to suck a reagent, while the reagent dispensing probe 22 approaches to the same reagent disk in an even-numbered cycle to suck a reagent. Accordingly, the two probes do not simultaneously approach to the reagent disk in the same cycle. Similarly, the reagent dispensing probe 23 approaches to the reagent disk 42 in an odd-numbered cycle to suck a reagent, while the reagent dispensing probe 21 approaches to the same reagent disk in an even-numbered cycle to suck a reagent. Accordingly, the two probes do not simultaneously approach to the reagent disk in the same cycle. It is, therefore, possible to shorten the time of each cycle and hence, to increase the number of samples to be analyzed per unit time.

In a single cycle, regents are sucked with only one reagent dispensing probe from the respective reagent disks. It is, therefore, possible to set longer the reagent-sucking time and probe-moving time and hence, to stably dispense the reagents with high accuracy.

The two reagent disks can rotate independently with each other, and in a single cycle, reagents are sucked with only one reagent dispensing probe from the respective reagent disks. It is, therefore, possible to freely choose a combination of regents to be sucked at the same time and hence, to perform an analysis with such a high analytical capacity as permitting the analysis even in the case of an irregular combination of analysis items.

In this embodiment, a first reagent and a second reagent are both sucked from the reagent disk 41 in an odd-numbered test, and a first reagent and a second reagent are both sucked from the reagent disk 42 in an even-numbered test. Accordingly, the first reagent and the second reagent, which are to be used for the same test item, can be mounted on the reagent disk. It is, therefore, only necessary to perform reagent replacements to the same reagent disk. This can reduce the labor for the reagent replacement, and can also decrease potential errors.

In this embodiment, two reagents can be received in the same reagent container 40. Therefore, the first reagent and second reagent, both of which correspond to a single test item, can be received in the same one of the reagent containers 40, and the first reagent and second reagent can be replaced at once. This can reduce the labor for the reagent replacement, and can also decrease potential errors.

In this embodiment, the reagent dispensing probe 20 approaches to the first-timing reagent dispensing position on the reaction disk 36 in an even-numbered cycle to inject the first reagent, while the reagent dispensing probe 21 approaches to the same reagent dispensing position in an odd-numbered cycle to inject the first reagent. Accordingly, the two probes do not simultaneously approach to the first-timing reagent dispensing position in the same cycle. Similarly, the reagent dispensing probe 22 makes an access to the second-timing reagent dispensing position and the third-timing reagent dispensing position on the reaction disk 36 in odd-numbered cycles to inject the second reagent, while the reagent dispensing probe 23 approaches to the same reagent dispensing positions in even-numbered cycles to inject the second reagent. Accordingly, the two probes do not simultaneously approach to the same reagent dispensing position in the same cycle. Further, the first-timing reagent dispensing position, the second-timing reagent dispensing position and the third-timing reagent dispensing position are apart from one another, so that the probes can simultaneously approach to the individual positions. It is, therefore, necessary to allocate only one reagent-injecting time per cycle and hence, to shorten each cycle time and to increase the number of samples analyzable per unit time.

Further, only one probe injects a reagent at a specific position in a single cycle. It is, therefore, possible to set longer the time usable for the injection and hence, to conduct the injection with high reproducibility and high accuracy. The reagents can hence be dispensed in highly accurate amounts, thereby permitting a high-accuracy analysis.

In this embodiment, the reagent dispensing probe 20 and reagent dispensing probe 23 suck reagents in an odd-numbered cycle and inject them in an even-numbered cycle, while the reagent dispensing probe 21 and reagent dispensing probe 22 suck reagents in an even-numbered cycle and inject them in an odd-numbered cycle. With respect to each probe, it is hence required perform a reagent sucking, a reagent injection and probe washing in the time of two cycles. The operation time can be set sufficiently long to ensure stable performance of the operation.

As the operation time of each reagent dispensing probe can be set long, a broad movable range can be set for the probe. As a consequence, the reagent disks can be dimensioned large, and reagents required for various types of tests can all be mounted on the reagent disks.

In this embodiment, the reagent dispensing probe 20 and the reagent dispensing probe 21 are common in the injecting position. The first reagent can be dispensed at an equivalent timing no matter through which one of the probes the first reagent is injected. It is, therefore, possible to analyze the course of a reaction under equal conditions.

In this embodiment, the reagent dispensing probe 22 and the reagent dispensing probe 23 can move in a direction perpendicular to the rail 26, and can approach to the common second-timing reagent dispensing position and third-timing reagent dispensing position to inject the second reagents, respectively. It is, therefore, possible to analyze plural reactions different from one another in the mixing timing of the second reagent and hence to increase the kinds of analyzable items.

Further, the reagent dispensing probe 22 and the reagent dispensing probe 23 are common to each other in the injecting position, thereby permitting analyses under equivalent conditions.

The reagent dispensing probe 20 and the reagent dispensing probe 21 are on the common rail 25, and the reagent dispensing probe 22 and the reagent dispensing probe 23 are on the common rail 26. A smaller area is, therefore, needed for the installation of the probes so that the analyzer can be constructed compact.

The reagent disk 41 and the reagent disk 42 are located on the outer and inner sides of the reaction disk 36, respectively, with the reagent dispensing positions on the reaction disk being located between the reagent disk 41 and the reagent disk 42. Accordingly, the two reagent disks can be arranged at a small interval therebetween, and as the rails 25,26 to be arranged over the two reagent disks and the reagent injecting positions, short rails can be used. The analyzer can therefore be constructed compact.

As the reagent disk 41 and the reagent disk 42 are arranged close to each other, the distances to the common reagent injection positions are short and therefore, the moving distances of the reagent dispensing probes are short. It is, therefore, possible to shorten the cycle time and hence, to increase the number of samples analyzable per unit time.

In this embodiment, the sampling probe 15 and the sampling probe 16 alternately repeat a sample sucking operation and a sample injection operation so that in a single cycle, only one sampling probe approaches to the sample container 10 and the reaction cell 35. It is, therefore, possible to shorten the cycle time and hence, to increase the number of samples analyzable per unit time.

It is only necessary for the sampling probe 15 and the sampling probe 16 to perform the sucking operation and injection operation of a sample and its washing in two cycles. The dispensing and probe movements can, therefore, be performed with a margin time, the accuracy of each dispensed amount can be heightened, and the accuracy of the analysis can be increased.

In this embodiment, to a sample dispensed by the sampling probe 15, the first reagent is dispensed by the reagent dispensing probe 20 from the reagent disk 41 and the second reagent is dispensed by the reagent dispensing probe 22 from the reagent disk 41. To a sample dispensed by the sampling probe 16, on the other hand, the first reagent is dispensed by the reagent dispensing probe 21 from the reagent disk 42 and the second reagent is dispensed by the reagent dispensing probe 23 from the reagent disk 42. Accordingly, the sampling probe 15, the reagent disk 41, the reagent dispensing probe 20 and the reagent dispensing probe 22 are combined into a first set, while the sampling probe 16, the reagent disk 42, the reagent dispensing probe 21 and the reagent dispensing probe 23 are combined into a second set, and none of them are combined with a set other of the first and second sets. For analysis items corresponding to the reagents arranged on the reagent disk 41, it is hence necessary to conduct only a calibration which makes use of the sampling probe 15, the reagent dispensing probe 20 and the reagent dispensing probe 22. For analysis items corresponding to the reagents arranged on the reagent disk 42, on the other hand, it is hence necessary to conduct only a calibration which makes use of the sampling probe 16, the reagent dispensing probe 21 and the reagent dispensing probe 23. It is, therefore, necessary to conduct calibrations with the individual sets only. The number of calibrations can, therefore, be reduced to avoid wasting of the reagents and time and also to avoid occurrence of any difference in the result of an analysis due to differences in characteristics among the probes.

If the first timing of reagent dispensing and the second or third timing of reagent dispensing were shifted from each other by an even number of cycles, it would be necessary to suck the first reagent and the second reagent in the same cycle. In this embodiment, however, the first timing of reagent dispensing and the second or third timing of reagent dispensing are shifted from each other by an odd number of cycles, so that the cycle in which the first reagent is sucked and a cycle in which the second reagent is aspirated are alternately repeated.

In this embodiment, there are fifty-four reaction cells 35, which rotate over 11 pitches in a cycle. Each reaction cell, therefore, rotates 360 degrees plus 1 pitch in 5 cycles. Accordingly, it will be 5 cycles later that the reaction cell located at a given position on the reaction disk moves to the adjacent position which is apart from the given position by 1 pitch. If the reaction disk were constructed such that each reaction cell would rotate 360 degrees plus 1 pitch in an even number of cycles, it would be the even number of cycles later that the reaction cell would move to the adjacent position which is apart by 1 pitch. In this case, positions to which each reaction cell would successively move at a time interval equivalent to the even number of cycles would be located side by side. If one attempts to allocate the timing, at which the first reagent is dispensed, and the timing, at which the second reagent is dispensed, to even numbers of cycles and odd numbers of cycles, respectively, in the above-mentioned case, the positions at which they are injected, respectively, would become apart from each other. It would, therefore, be necessary to arrange the reagent dispensing probes at positions which are apart from each other. In this embodiment, however, the reaction disk is constructed such that each reaction cell rotates 360 degrees plus 1 pitch in an odd number of cycles. It is, therefore, possible to arrange the positions—at which the first reagent and the second positions are injected, respectively—close to each other, and hence, to construct the analyzer in a small size. Construction of the reaction disk such that each reaction cell rotates 360 degrees minus 1 pitch in an odd number of cycles can also bring about the same advantageous effect.

In this embodiment, the reaction disk is constructed such that the position of each reaction cell is shifted by 1 pitch in an odd number of cycles. Accordingly, a train of reaction cells, which cannot be measured as they pass at an accelerated or decelerated speed through the measurement position by the detection unit 51, occurs at successive timings. Since these successive timings can be brought into agreement with the reaction-cell-washing timings which are irrelevant to the measurement of the courses of reactions, these courses of reactions can be continuously analyzed without any timing at which no measurement is feasible. It is, therefore, possible to perform analyses of a wide variety of items ranging from items each of which requires only a short time for its reaction to items each of which requires a long time for its reaction.

In a modified embodiment, the reaction disk 36 rotates clockwise over 43 pitches per cycle in an analyzer of a similar construction as that illustrated in FIGS. 1, 2 and 3. In this modified embodiment, a reaction cell located at Position 1 on the reaction disk also moves to Position 2 on the reaction disk in the next cycle. As the reaction cell passes through the position of the detection unit 51 four times in 5 cycles in this case, the reaction cell can be measured repeatedly. It is, therefore, possible to perform an analysis at high accuracy.

Figure 4:
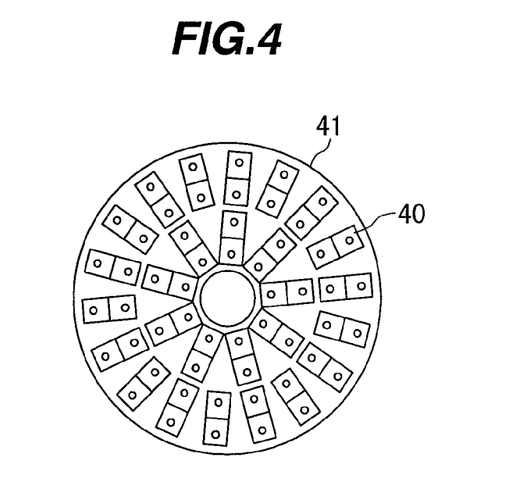
FIG. 4 is a construction diagram of a reagent disk in an automatic analyzer according to a second embodiment of the present invention.

FIG. 4 shows a reagent disk of the second embodiment of the present invention. In this embodiment, reagent containers 40 are arranged at double circles on the reagent disk 41. Reagent containers are similarly arranged on the reagent disk 42. As this embodiment makes it possible to arrange many reagents on small reagent disks, the number of analyzable items can be increased without making the size of the analyzer larger.

Figure 5:
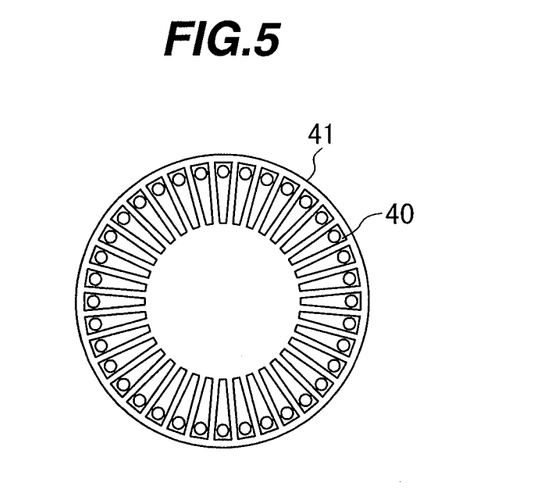
FIG. 5 is a construction diagram of a reagent disk in an automatic analyzer according to a third embodiment of the present invention.

FIG. 5 shows a reagent disk of the third embodiment according to the present invention. In this embodiment, reagent containers 40 have a sectorial shape, and one reagent is received in one container. Reagent containers of this shape are mounted on both of the reagent disk 41 and reagent disk 42. In this embodiment, the arrangement of the reagent containers on and along the circular circumference of the reagent disk makes it possible to reduce the spaces between the adjacent reagent containers. The individual reagent containers can, therefore, be increased in capacity so that more samples can be analyzed without replacing the reagent containers. Further, number of items to be analyzed can be increased without enlarging the size of an automatic analyzer.

Figure 6:
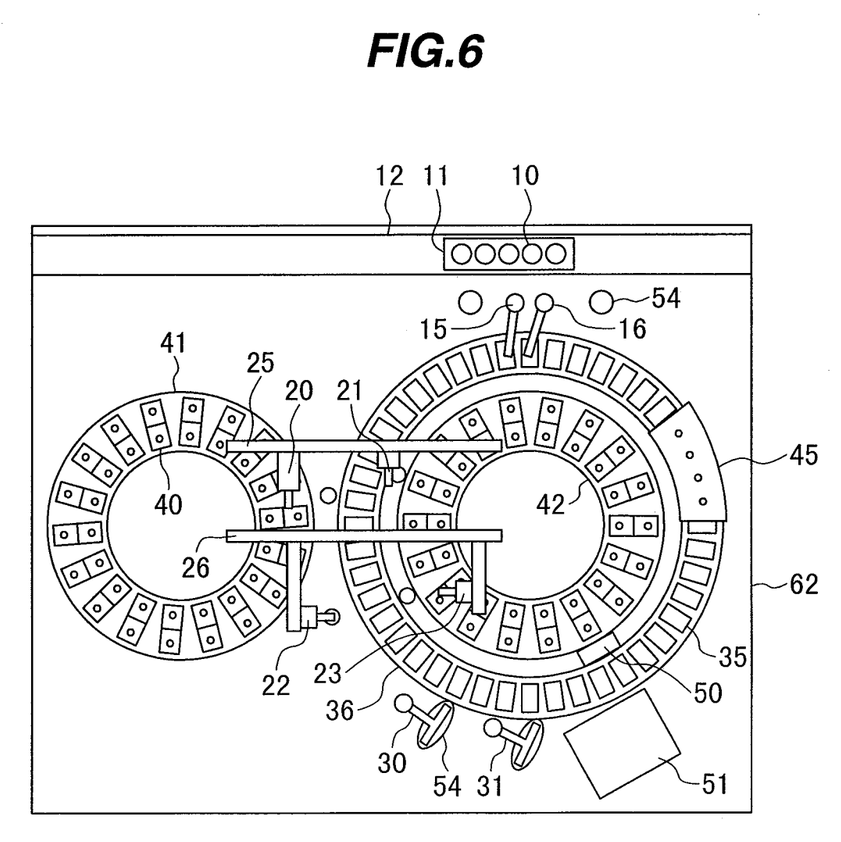
FIG. 6 is a top plan view of an automatic analyzer according to a fourth embodiment of the present invention.

FIG. 6 shows a top view of the fourth embodiment according to the present invention. The automatic analyzer shown in FIG. 6 is different from an automatic analyzer shown in FIG. 2 in that the sampling probe 15 and the sampling probe 16 inject samples into reaction cells located at adjacent positions with each other, that the reagent dispensing probe 20 and the reagent dispensing probe 21 inject reagents into reaction cells located at adjacent positions with each other, that the reagent dispensing probe 22 and the reagent dispensing probe 23 inject reagents into reaction cells located at adjacent positions with each other, and the mixing unit 30 and the mixing unit 31 include two mixing bars respectively to agitate the liquids in adjacent two reaction cells at the same time.

The automatic analyzer of this embodiment operates as will be described next. The sampling probe 15 and the sampling probe 16 suck samples from sample containers 10 at the same time, and inject them into reaction cells located at adjacent positions with each other on the reaction disk 36. In the next cycle, the reagent dispensing probe 20 and the reagent dispensing probe 21 inject the corresponding first reagents into the respective reaction cells. In the following cycle, the mixing unit 30 mixes the liquids in the individual reaction cells at the same time. After their optical measurements are then repeated a few times, the reagent dispensing probe 22 and the reagent dispensing probe 23 inject the second regents into the respective reaction cells.

In this embodiment, the injections of samples and reagents which relate to tests to be conducted in two reaction cells are performed at the same time with the reaction cells arranged adjacent with each other. It is, therefore, possible to increase the number of samples analyzable per unit time.

In this embodiment, the injections of the samples by the two sampling probes, the injections of the first reagents by the corresponding reagent dispensing probes arranged in combination, and the injections of the second reagents by the corresponding reagent dispensing probes arranged in combination are each performed to the adjacent reaction cells located very close to each other. It is, therefore, possible to construct the analyzer compact.

In this embodiment, the first reagent and the second reagent for the sample dispensed by the sampling probe 15 can be arranged together on the reagent disk 41, while the first reagent and the second reagent for the sample dispensed by the sampling probe 16 can be arranged together on the reagent disk 42. This can simplify the replacement of reagent containers, and can avoid potential errors in replacing reagent containers.

Figure 7:
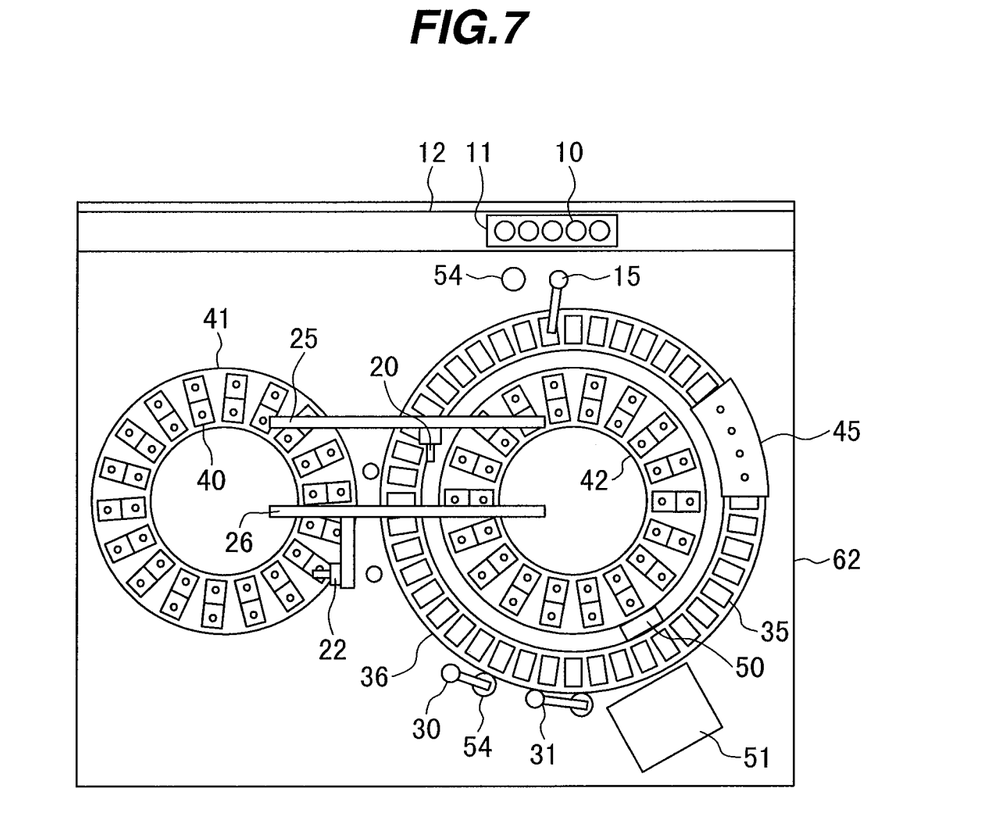
FIG. 7 is a top plan view of an automatic analyzer according to a fifth embodiment of the present invention.

FIG. 7 shows a top view of the fifth embodiment according to the present invention. The automatic analyzer shown in FIG. 7 is different from the automatic analyzer shown in FIG. 2 in that the former automatic analyzer is provided with only one sampling probe, only one reagent dispensing probe on the rail 25 and only one reagent dispensing probe on the rail 26.

The automatic analyzer of this embodiment operates as will be described next. The sample in a sample container 10 is dispensed by the sampling probe 15 into a reaction cell 35 on the reaction disk 36. In an even-numbered cycle, the reagent dispensing probe 20 sucks a reagent from the reagent disk 41 and injects it into a reaction cell, while the reagent dispensing probe 22 sucks a reagent from the reagent disk 42 and injects it into a reaction cell. In an odd-numbered cycle, the reagent dispensing probe 20 sucks a reagent from the reagent disk 42 and injects it into a reaction cell, while the reagent dispensing probe 22 sucks a reagent from the reagent disk 41 and injects it into a reaction cell. As the first-timing reagent dispensing position and the second-timing reagent dispensing position are apart from each other by an odd number of cycles, a reagent to be dispensed at the first timing in a test and another reagent to be dispensed at the second or third timing in the same test are always supplied from the reagent disk on the same side.

In this embodiment, the reagent dispensing probe 20 and the reagent dispensing probe 22 each aspirates reagents from both of the reagent disk 41 and the reagent disk 42. This embodiment, therefore, requires the smaller number of reagent dispensing probes, thereby allowing to provide the analyzer at lower price.

In this embodiment, an analysis making use of reagents arranged on the reagent disk 41 and an analysis making use of reagents arranged on the reagent disk 42 are each performed by the common reagent dispensing probes and the common sampling probe. It is, therefore, possible to obtain analysis results of high reproducibility irrespective of the characteristics of the individual probes.

In this embodiment, the aspirations of reagents from the respective reagent disks in each cycle are performed by the corresponding reagent dispensing probes, respectively. It is, therefore, possible to set the time of each cycle longer and also to increase the number of samples analyzable per unit time.

According to the present invention, plural reagent disks, for example, two reagent disks with a first group of reagents and a second group of reagents mounted thereon, respectively, are disposed, and during a single cycle, one of the first group of reagents and one of the second group of reagents are aspirated from the corresponding reagent disks by only a single reagent dispensing probe. It is, therefore, possible to provide an automatic analyzer, which can mount many reagents and has a high analytical capacity per unit time.

What is claimed is:

1. An automatic analyzer, comprising:
    reagent disks including a first reagent disk and a second reagent disk, plural reagent containers being arranged on a circumference of each of said first reagent disk and second reagent disk, said plural reagent containers including a first reagent container and second reagent container, said first reagent container receiving a first reagent to be dispensed at a first timing, said second reagent container receiving a second reagent to be dispensed at a second timing or a third timing;
    a reaction disk arranging plural reaction cells on a circumference thereof;
    an analysis section for analyzing reactions of samples and reagents received in said reaction cells;
    a first reagent dispensing probe which sucks said first reagent for said first reagent disk;
    a second reagent dispensing probe which sucks said second reagent for said second reagent disk;
    a third reagent dispensing probe which sucks said first reagent for said second reagent disk;
    a fourth reagent dispensing probe which sucks said first reagent for said first reagent disk; and
    a controller, the controller configured to:
    control said first reagent dispensing probe to suck said first reagent in said first reagent container on said first reagent disk, and control said first reagent dispensing probe to inject said first reagent into said reaction cell positioned on a first injection position of said reaction disk in an even number cycle of rotation cycles of said reaction disk;
    control said second reagent dispensing probe to suck said second reagent in said second reagent container on said second reagent disk, and control said second reagent dispensing probe to inject said second reagent into said reaction cell positioned on a second injection position of said reaction disk in an even number cycle of rotation cycles of said reaction disk;
    control said third reagent dispensing probe to suck said first reagent in said first reagent container on said second reagent disk, and control said third reagent dispensing probe to inject said first reagent into said reaction cell positioned on the first injection position of said reaction disk in an odd number cycle of rotation cycles of said reaction disk; and
    control said fourth reagent dispensing probe to suck said second reagent in said second reagent container on said first reagent disk, and control said fourth reagent dispensing probe to inject said second reagent into said reaction cell positioned on the second injection position of said reaction disk in an odd number cycle of rotation cycles of said reaction disk,
    wherein the first injection position is located between locations where the first reagent probe sucks the first reagent and where the third reagent probe sucks the first reagent, and
    wherein the second injection position is located between locations where the second reagent probe sucks the second reagent and where the fourth reagent probe sucks the second reagent.

2. The automatic analyzer according to claim 1, wherein said controller is configured to control said reaction disk to rotate so that a predetermined reaction cell is moved from said first reagent injection position to said second reagent injection position while said reaction disk moves with a predetermined odd number of cycles.

3. The automatic analyzer according to claim 1, further comprising:
    a first sample probe which injects a sample into said reaction cell; and
    a second sample probe which injects a sample into said reaction cell,
    wherein the controller is configured to:
    control said first sample probe to inject a sample into said reaction cell at said odd number cycle, and
    control said second sample probe to inject a sample into said reaction cell at said even number cycle,
    wherein said first reagent dispensing probe and said fourth reagent dispensing probe inject the first reagent and the second reagent, respectively, into said reaction cell receiving said sample injected from said first sample probe, and said third reagent dispensing probe and said second reagent dispensing probe inject the first reagent and second reagent, respectively, into said reaction cell receiving said sample injected from said second sample probe.

* * * * *

UNITED STATES PATENT AND TRADEMARK OFFICE
CERTIFICATE OF CORRECTION

PATENT NO. : 8,496,877 B2
APPLICATION NO. : 13/529395
DATED : July 30, 2013
INVENTOR(S) : I. Yamazaki et al.

It is certified that error appears in the above-identified patent and that said Letters Patent is hereby corrected as shown below:

In the Claims

Column 11, line 65, delete "first" and substitute --second--.

Signed and Sealed this
Eleventh Day of February, 2014

Michelle K. Lee
*Deputy Director of the United States Patent and Trademark Office*